United States Patent [19]

Marguerie de Rotrou et al.

[11] Patent Number: 5,565,358
[45] Date of Patent: Oct. 15, 1996

[54] ENHANCER AND SILENCER SEQUENCES ISOLATED FROM THE GPIIB PROMOTER

[75] Inventors: Gérard Marguerie de Rotrou, Vitry-sur-Seine; Georges Uzan, Grenogle; Marie-Hélène Prandini, Gieres, all of France

[73] Assignees: Commissariat a l'Energie Atomique (C.E.A.); Institut National de la Sante et de la Recherche Medicale (I.N.S.E.R.M.), both of Paris Cedex, France

[21] Appl. No.: 317,648

[22] Filed: Sep. 30, 1994

Related U.S. Application Data

[63] Continuation of Ser. No. 974,600, filed as PCT/FR92/00596, Jun. 26, 1992, published as WO93/00438, Jan. 7, 1993, abandoned.

[30] Foreign Application Priority Data

Jun. 28, 1991 [FR] France .................................. 91 08039

[51] Int. Cl.$^6$ .......................... C12N 15/09; C12N 15/63; C12N 15/85; C07H 21/04
[52] U.S. Cl. ............... 435/320.1; 435/69.1; 435/172.1; 435/172.3; 435/240.1; 435/240.2; 435/252.3; 536/23.1; 536/23.2; 536/23.5; 536/24.1
[58] Field of Search ................... 435/69.1, 172.1, 435/172.3, 240.1, 240.2, 252.3, 320.1; 536/23.1, 23.2, 23.5, 24.1

[56] References Cited

U.S. PATENT DOCUMENTS 4,740,461  4/1988  Kaufman ............................. 435/69.1

OTHER PUBLICATIONS

Journal of Biological Chemistry. vol. 267, No. 15, May 25, 1992, Baltimore, US, pp. 10370–10374; Prandini, M. H. et al.: "Characterization of a specific erythromegakaryocytic enhancer within the glycoprotein IIb promoter".

Biochemical and Biophysical Research Communications., vol. 156, No. 1, 14 Oct. 1988, Duluth, MN, US. pp. 595–601; Prandini, M. H., et al.: "Isolation of the human characterization of the 5' flanking region".

Biochemistry, vol. 29, No. 5, 1990, Easton, Pa US, pp. 1232–1244; Heidenreich, R. et al.: "Organization of the gene for platelet glycoprotein IIb".

Struhl (1981) Proceedings of the National Academy of Sciences vol. 78, pp. 4461–4465.

van Zonneveld et al. (1988) Proceedings of the National Academy of Sciences, vol. 85, pp. 5525–5529.

Dynan (1989) Cell, vol. 58, pp. 1–4.

Wasylyk (1988) Biochimica et Biophysica Acta, vol. 951, pp. 17–35.

Rusconi (1991) Experientia, vol. 47, pp. 866–877.

Brand et al. (1985) Cell, vol. 41, pp. 41–48.

Uzan et al. (1991) Journal of Biological Chemistry, vol. 266, pp. 8932–8939.

Romero et al. (1990) Nature, vol. 344, pp. 447–449.

Primary Examiner—Mindy Fleisher
Assistant Examiner—Nancy J. Degen
Attorney, Agent, or Firm—Oblon, Spivak, McClelland, Maier, & Neustadt, P.C.

[57] ABSTRACT

An amplifier sequence and a silencer sequence of the GPIIb promoter are disclosed. The amplifier sequence includes sequence domains (I) and (II), and the silencer sequence includes sequence domain (III). The use of these sequences in genetic engineering is also described.

22 Claims, 3 Drawing Sheets

ENHANCER AND SILENCER SEQUENCES ISOLATED FROM THE GPIIB PROMOTER

This application is a continuation of application Ser. No. 07/974,600, filed Feb. 22, 1993, abandoned, which was filed as International Application No. PCT/FR92/00596 on Jun. 26, 1992, and published as WO93/00438 on Jan. 7, 1993.

The invention relates to sequences regulating the expression of a gene, which are isolated from the promoter of the gene encoding the protein GPIIb.

The protein GPIIb corresponds to the α subunit of a surface protein of blood platelets called GPIIb-IIIa. The protein GBIIb-IIIa, which belongs to the family comprising integrins, is a receptor which is specific for fibrinogen, fibronectin and Von Willebrand factor.

While the β subunit (GPIIIa) of this integrin is expressed in various cell types (megakaryocytes, endothelial cells, macrophages, fibroblasts and the like), the GPIIb subunit is expressed only in megakaryocytes which are the precursor cells of blood platelets. For this reason, it has been proposed to use this protein within the framework of studies on the mechanisms of hematopoiesis, specifically to study megakaryocytopoiesis.

During their previous research studies, the inventors cloned the human GPIIb gene [PRANDINI et al., Biochem. Biophys. Res. Commun. 156, 595–601, (1988)]. They studied, more particularly, the region flanking in 5', the sequence encoding GPIIb, and they identified a sequence of about 1.1 kb, upstream of the GPIIb initiation codon, which acts as a promoter.

Subsequently, in order the characterize the activity of this promoter, they produced constructs in which a CAT reporter gene (gene encoding chloramphenicol-acetyl-transferase) was placed under the control of said promoter. The results of this work are disclosed in the article by UZAN et al. [J. Biol. Chem., 266, 14, 1932–1939, (1991)]. This work made it possible to identify various promoter regions which interact with nuclear factors which bind to DNA. In particular, they identified a region centered around the nucleotide –54 (the positions of the nucleotides are located starting from the first base of the GPIIb-encoding sequence), which is similar to the binding site of a type E1 nuclear factor, a region located around –233 which contains a consensus sequence CCAAT (which is similar to the binding site, CAAT, existing in the α-globin gene). They also located two domains centered around positions –345 and –540 respectively, which bind ubiquitous proteins which are present in various types of cells.

Finally, they located two other domains centered around positions –460 and –510 respectively, which interact with proteins which are present only in megakaryotic cells. Furthermore, they observed that deletion of the region containing these two domains induces a substantial decrease in the activity of the promoter (of the order of 60% to 70%).

This region therefore appears to contain a positive regulatory sequence specific to megakaryocytes. The identification of such regulatory regions is of great practical importance insofar as it makes it possible to envisage modifying the regulation of the genes present in the megakaryocytes or introduced into them by genetic engineering. This makes it possible to obtain valuable models for elucidating the mechanism of thrombopoiesis and of the etiology of thrombosis both in vitro, in cell cultures, and in vivo, for example in transgenic animals. However, it is necessary, in order to be able to use the properties of such regulatory sequences, to know both their location and their mechanism of action.

The inventors, in pursuing their work, have now demonstrated the role of some of the regulatory sequences present in the GPIIb promoter and, furthermore, they have identified new sequences which have a regulatory function.

Thus, they observed that a 192-bp DNA fragment, corresponding to the sequence situated between position –598 and position –406 and comprising the domains D and E for the binding of nuclear proteins, contained an enhancer domain. Indeed, they showed that the properties of this fragment, with respect to the increase in the expression of the gene, are conserved regardless of its orientation and its location relative to the promoter, and that this enhancer domain is active both on the GPIIb promoter and on a heterologous promoter. This enhancer domain is active both on the GPIIb promoter and on a heterologous promoter. They also showed that the two domains D and E were required for the activity of the enhancer. Finally, the inventors observed that, contrary to what was thought up until now, this enhancer was not active solely in the megakaryocytes, but also in erythrocytic cell lines.

Furthermore, the inventors located in the GPIIb promoter a new domain whose function had not been suspected up until now. This domain, which is situated in the sequence between positions –78 and –107 of the GPIIb promoter, has a silencer type function; this silencer is inactive in the megakaryocytic cell lines.

The inventors also identified a sequence between positions –29 and –13 of the GPIIb promoter and which contains a domain whose presence is essential to bring about the non-tissue-specific basal expression of this promoter.

The subject of the present invention is a DNA sequence which constitutes an enhancer for controlling the expression of a gene in erythrocytic or megakaryocytic cell lines, which sequence comprises two domains:

a domain comprising a homologous sequence of the following sequence (I; SEQ ID NO: 1):

5' TCCT AGAAGGAGGAAGT GGGT AAATG 3'  (I)
3' AGGATCTTCCTCCTTCACCCATTTAC 5' and a domain comprising a homologous sequence of the following sequence (II; SEQ ID NO: 2):

5' CTCAGGTTTTATCGGGGGC AGC AGCT 3'  (II)
3' GAGTCC AAAAT AGCCCCC GTC GTCGA 5'.

The sequence I is that of the domain (E) situated between positions –526 and –501 of the GPIIb promoter, the sequence II is that of the domain (D) situated between positions –476 and –451 of the GPIIb promoter.

Within the context of the present invention, homologous sequence is understood to mean any sequence differing from the sequences of the invention by only the substitution, deletion or addition of a small number of bases, provided, of course, that these sequences conserve the essential functional properties of the sequences of the invention. In the case of the abovementioned sequences, it is essential that the following are conserved: for the sequence I, the unit:
GG
CC
(corresponding to positions –515 and –516 of the GPIIb promoter), and for the sequence II, the unit:
TC
AG
(corresponding to positions –463 and –464 of the GPIIb promoter); these units are indeed essential for the enhancer activity.

According to a preferred embodiment of the enhancer sequence conforming to the invention, it consists of a sequence homologous to that of the DNA fragment situated between positions –599 and –405 of the GPIIb promoter.

The subject of the invention is also a DNA sequence which constitutes a silencer, which inhibits the effect of the enhancer sequence defined above, and which is inactive in the megakaryocytic cell lines, which sequence comprises a sequence homologous to the following sequence (III; SEQ ID NO: 3)

> 5' GCCCTTTGCTCTGCCCGTTG 3'  (III)
> 3' CGGGAAACGAGACGGGCAAC 5'.

According to a preferred embodiment of a silencer sequence conforming to the invention, it consists of a sequence homologous to the following sequence (IV; SEQ ID NO: 4):

> 5' CTATAGCCCTTTGCTCTGCCCGTTGCTCAG 3'  (IV)
> 3' GATATCGGGAAACGAGACGGGCAACGAGTC 5'.

The sequence III corresponds to the sequence between −102 and −83 in the GPIIb promoter.

The sequence IV corresponds to the sequence between −107 and −78 in the GPIIb promoter.

The subject of the invention is also recombinant DNA fragments comprising at least one copy of an enhancer sequence as defined above, and/or at least one copy of a silencer sequence as defined above.

The recombinant DNA fragments are intended to serve as base for other constructs, in which they are associated with a promoter under whose control it is desired to express a gene, in particular in erythrocytic or megakaryocytic cell lines.

The subject of the invention is also recombinant vectors (viruses, plasmids and the like) containing at least one recombinant DNA fragment as defined above, optionally associated with a promoter and with a gene which it is desired to express under the control of said promoter.

The subject of the invention is also prokaryotic or eukaryotic cells transformed by at least one recombinant vector as defined above.

The invention finds many applications in the study and treatment of hematological diseases, and in particular thromboses, where it provides tools which makes it possible to study and to modify, where appropriate, the behavior of cell lines, in particular that of the erythrocytic line and the megakaryocytic line.

It also makes it possible to regulate, in a tissue-specific manner, the expression of various genes, by placing them under the control of the enhancer and/or silencer sequences, or on the contrary, by eliminating this control. It is for example conceivable to allow ubiquitous genes to be specifically expressed in blood platelets. These applications can be implemented both in vitro, in cell cultures, and in vivo, for example by making it possible to produce transgenic animals in which it would be possible to control thrombogenesis and thrombopoiesis.

The present invention will be understood more clearly with the aid of the additional description below, which refers to examples demonstrating the enhancer or silencer properties of the sequences conforming to the invention.

It should be clearly understood, however, that these examples are given solely by way of illustration of the invention and in no manner constitute a limitation thereof.

EXAMPLE 1

CHARACTERIZATION OF THE ENHANCER DOMAIN

Figure 1:
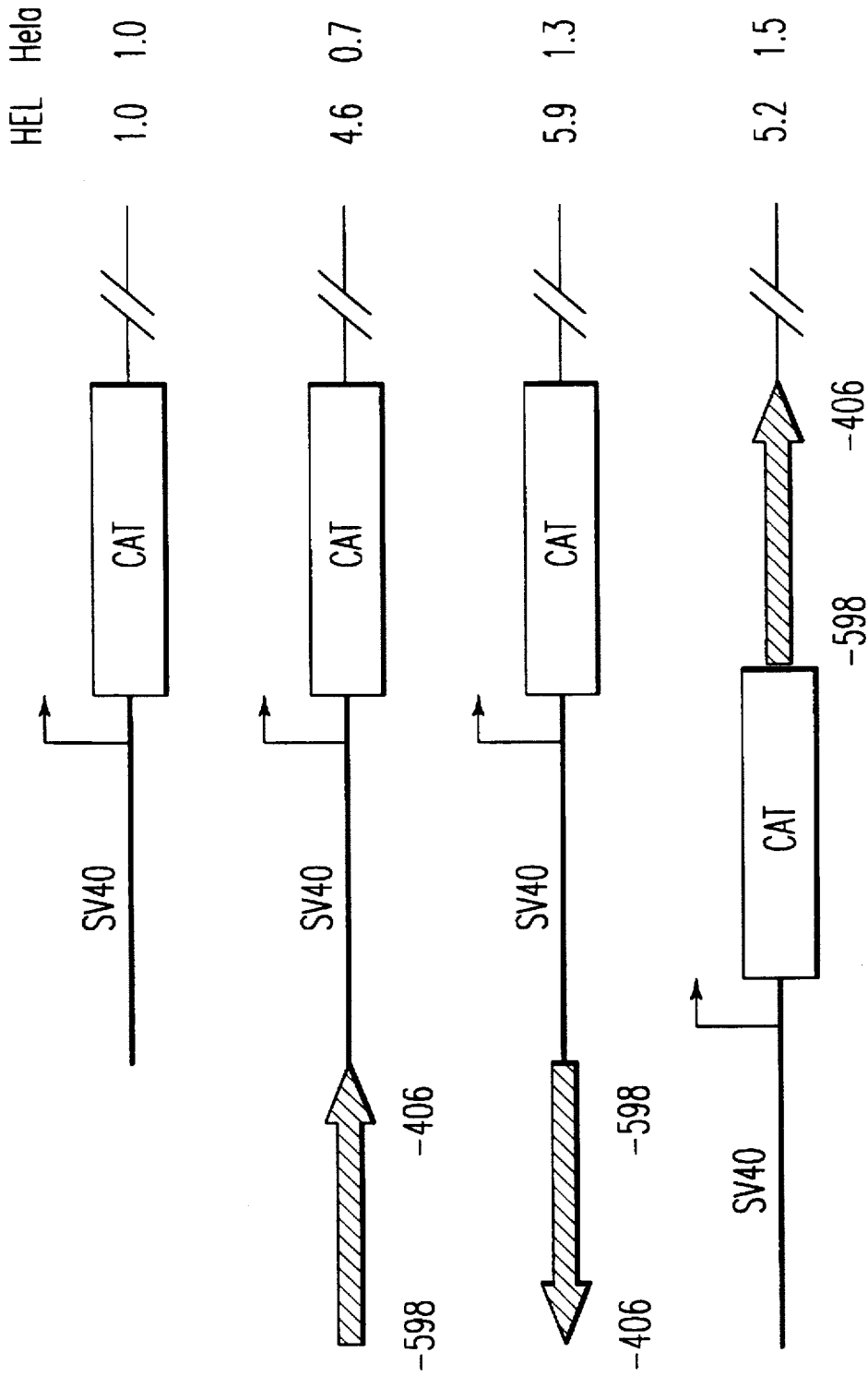
FIG. 1 shows the level of CAT activity in cells transfected with plasmids containing the 192-bp fragment.

A 192-bp HindIII/PvuI fragment, corresponding to the sequence between positions −598 and −406 of the GPIIb promoter, is inserted into the plasmid pBLCAT3 [LUCKLOW et al. Nucleic Acid. Res., 15, 1311–1326 (1987)]. Three different constructions are carried out. In two of them, the 192-bp fragment is inserted upstream of the SV40 promoter, either in the direct orientation, or in the reverse orientation. In the third construction, the 192-bp DNA fragment is inserted in the direct orientation, downstream of the CAT-encoding gene. The cells HEL (megakaryocytic type: this line is derived from an erythroid leukemia and has, nevertheless, numerous megakaryocytic characters; it expresses at its surface the complex GPIIb/IIIa over 90% of the cells), Hela (epithelial line) and K562 (erythrocytic type: this line possesses very distinct erythoid characters; it expresses glycophorin A and various globin chains; it does not express GPIIb/IIIa) are transfected with the plasmids obtained. A control is prepared by transfecting the same cells with the plasmid pBLCAT3. The CAT activity is measured in all the cells (the value 1 is arbitrarily attributed to the CAT activity measured in the cells transfected with the plasmid pBLCAT3). Under these conditions, the HEL and K562 cells transfected with the plasmids containing the 192-bp fragment have an increased CAT activity (varying between 3.6 and 6.3), while the Hela cells transfected with the same plasmids have an activity similar to that of the control cells (0.7 to 1.6) (FIG. 1).

It is therefore evident that the 192-bp DNA fragment increases the activity of a promoter (SV40 promoter), and does so, independently of its position and its orientation; it therefore possesses the characteristics of an enhancer. It is, furthermore, an enhancer which is specific for certain tissues given that it is active in the megakaryocytic and erythroid cell lines but not in the epithelial cells (Hela).

EXAMPLE 2

ANALYSIS OF THE ENHANCER REGION

It is known (UZAN et al., J. Biol. Chem., 266, 14, 1932–1939, (1991)) that two regions, called domain D and domain E respectively, which are present in the 192-bp fragment, interact with nuclear proteins present in megakaryocytes.

The inventors have now examined whether this interaction is connected with the enhancer activity and which regions of the domains D and E are more specifically involved in this interaction.

Synthetic oligonucleotides with sequences identical to those of the domains D and E were incubated with nuclear extracts of HEL cells. After incubation, these oligonucleotides were partially methylated and analyzed by gel migration. The DNA/protein complexes were eluted, fragmented using the MAXAM and GILBERT technique, and the fragments were analyzed on a polyacrylamide gel. This experiment makes it possible to show that in the domain D, nucleotides −463 and −464 are involved in DNA/protein binding, whereas in the domain E, nucleotides −516 and −515 are those which are involved.

Figure 2:
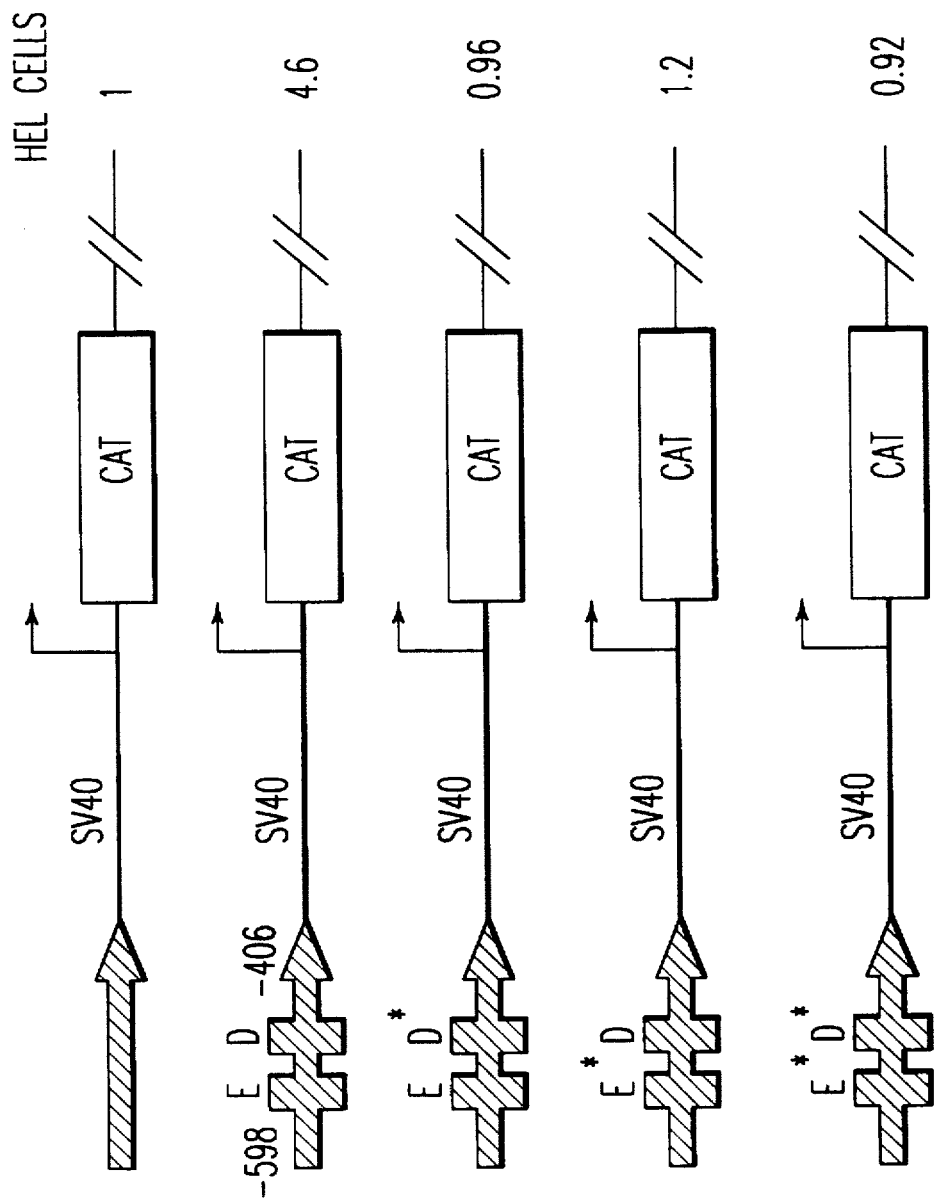
FIG. 2 shows the effects of mutations in domains D and E.

Mutation experiments regarding these nucleotides were therefore carried out [Mutations carried out in the phage M13 using the kit Oligonucleotide Directed In Vitro Mutagenesis, System Version 2, RPN 1523 (AMERSHAM)]. The results are illustrated by FIG. 2, which shows that a mutation, either in the domain E, or in the domain D, is enough to completely destroy the effect of the enhancer sequence; a mutation of both domains at the same time has no additional effect.

To verify that this observation, which was made in the case of a heterologous promoter, was also applicable when the enhancer was situated in the GPIIb promoter, the same mutations were introduced, separately or individually, into the plasmid called −813 containing a DNA fragment corresponding to the 813-bp sequence in 5' of the GPIIb initiation codon, which fragment is placed at the XbaI site of the plasmid pBLCAT3, upstream of the CAT-encoding sequence. Under this condition, a mutation in the domain D or in the domain E produces a 60% decrease in the CAT activity. This same decrease is observed when the 192bp fragment is excised from the construct. This shows that the domain D and the domain E are both required for the activity of the enhancer.

EXAMPLE 3

CHARACTERIZATION OF THE SILENCER SEQUENCE

Fragments of the promoter of the GPIIb gene are obtained by successive deletions of the 5' end of a −643/+33 DNA segment of the GPIIb gene, using an Exonuclease III as described by UZAN et al. (publication mentioned above). The fragments thus obtained are inserted into the vector pBLCAT3 at the XbaI upstream of the CAT gene, and this vector is used to transfect the HEL and Hela cells. As the deletions progressed, the inventors surprisingly observed that while the CAT activity in the HEL cells decreased (which corresponds to the loss of the enhancer sequence), a CAT activity appeared in the Hela cells. Starting from position −173, a gradual loss of tissue specificity was observed, the CAT activity being equivalent in the HEL cells and the Hela cells. The inventors therefore postulated the existence, in this promoter region, of a negative regulatory sequence and set out to characterize it.

Figure 3:
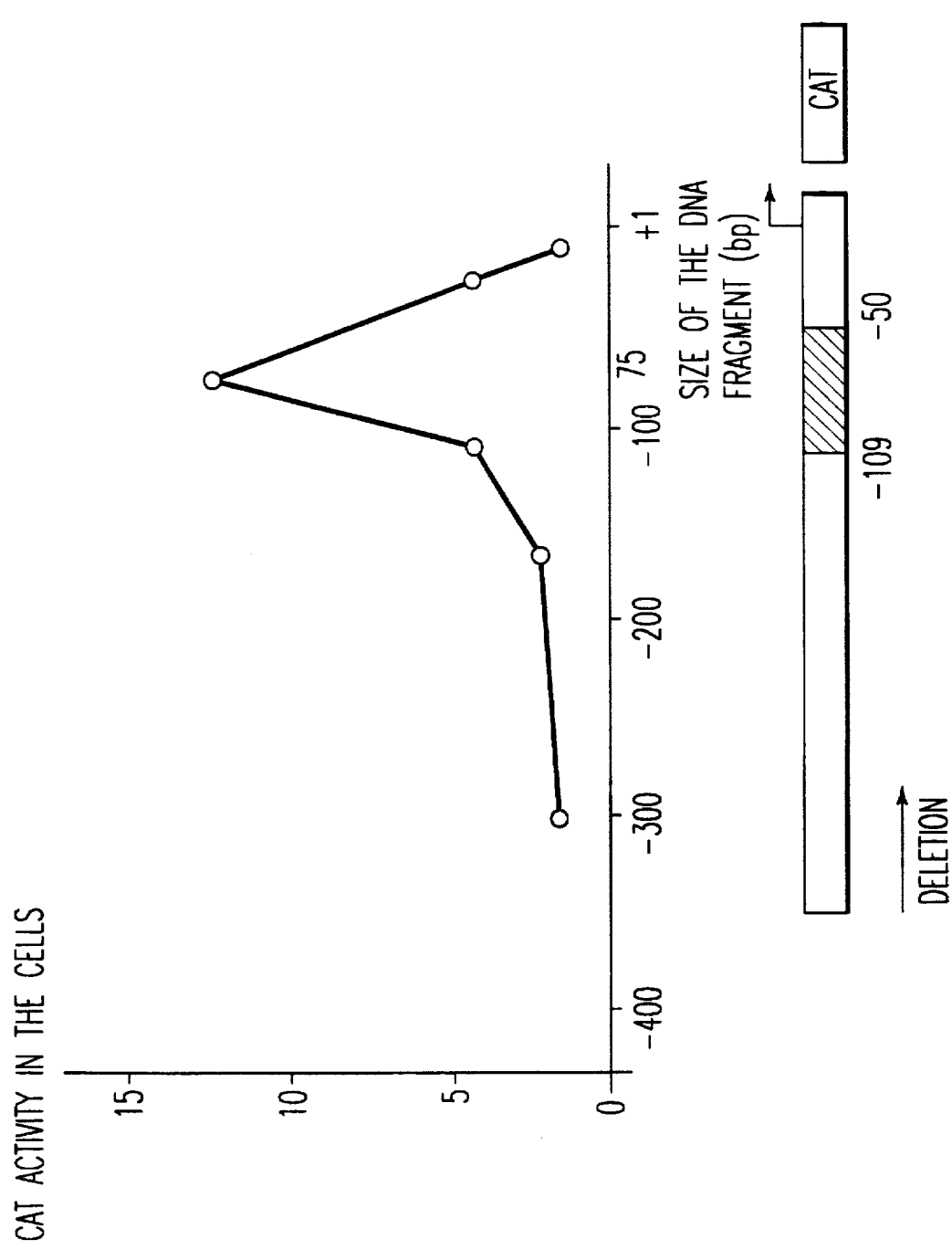
FIG. 3 shows the level of activity in cells transfected with deletion mutants.

For that, the mutants obtained by deletion of the 5' and, as described above, were used to transfect the K562 cell lines (this erythrocytic line does not express the GPIIb protein). FIG. 3 illustrates the results obtained. These results are expressed as relative CAT activity with respect to the activity obtained with a construct containing the −643/+33 fragment of the promoter region of the GPIIb protein (in this construct, the enhancer is not expressed in the K562 cells). The positions of the various deletions are indicated on the x-axis. These results show that the activity of the negative regulatory region decreases in the vicinity of position −170, this activity being minimal between positions −103 and −73.

In order to verify the role of this promoter region, the inventors carried out mutations in this region and in the regions immediately adjacent. The sequences of the fragments studied were replaced by other sequences bearing no relationship to each other, which were synthesized using the polymerase chain reaction as described in the publication by M. KAMMANN et al. [Nucleic Acid. Res. 17:13, 5404, (1989)]. The first amplification is carried out using on the plasmid pBLIIbCAT3 a 20-bp 5' primer from the plasmid pBLIIbCAT3 situated 80 bp upstream of the cloning site [the plasmid pBLIIbCAT3 is described by UZAN et al. (publication mentioned above)]. The 50-bp 3' primer contains the following regions:

2 sequences, each of 15 bp, homologous to those of the wild-type promoter, and which flank the region to be studied;

1 central region, of 20 bp, in which the sequence of the wild-type promoter is substituted by a completely different sequence.

This first amplification is carried out using 10 ng of the plasmid pBLIIbCAT3 as template. After purification, the DNA fragment obtained at the end of this first amplification stage is used as template for a second amplification, together with a 664-bp AccI-EcoRI fragment obtained from the plasmid pBLIIbCAT3. This fragment contains 280 bp of the CAT-encoding sequence. For this second amplification, a 3' primer is used which corresponds to a fragment of the CAT gene situated 140 bp downstream of the initiation site; the 5' primer is the same as that used in the first amplification.

Three types of mutants are thus produced:

the first, corresponding to the mutation of the sequence −83 to −102 of the GPIIb promoter, is called hereinafter IIb $S_1$;

the second, corresponding to the mutation of the sequence −63 to −82 of GPIIb, is called hereinafter IIb $S_2$;

and the third, corresponding to the mutation of the sequence −99 to −128, is called hereinafter IIb $S_3$.

These mutants are then introduced into the multisite linker of the plasmid pBLCAT3, in place of a fragment excised between the HindIII and BamHI sites.

The plasmids obtained are used to transfect the following cell lines: HEL, Hela, K562 and Nalm 6 (precursor line for the B lymphocytes).

The CAT activity is measured in the transfected cells:

In the case of the IIb$S_1$ mutants, no difference in activity is observed, in the HEL line, between the cells transfected with the mutant plasmid and the cells transfected with the wild-type plasmid; this is not the case in the cells of the K562, Hela and Nalm 6 lines where no CAT activity is observed when the cells are transfected with the wild-type plasmid, whereas this activity appears when the cells are transfected with the mutant plasmid.

In the case of the IIb$S_2$ and IIb$S_3$ mutants, the CAT activity is expressed in the HEL cells and is not expressed in the K562, Hela and Nalm 6 cells, whether these cells are transfected with the mutant plasmids or with the wild-type plasmid.

This shows that the −83/−102 region of the GPIIb promoter possesses (or contains a sequence possessing) a silencer type activity which hampers the enhancer activity in cells not belonging to the megakaryocytic line.

EXAMPLE 4

EXPRESSION OF THE LACZ GENE UNDER THE CONTROL OF THE GPIIB PROMOTER

1) The −782/+33 region of the GPIIb promoter was inserted into the vector pLACF [PESHON et al., Proc. Natl. Acad. Sci. USA, 84, 5316 (1987)] downstream of the LacZ gene encoding β-galactosidase.

The GPIIb promoter, cloned into the vector M13MP18, was digested in 5' by the enzyme SstI and in 3' by the enzyme BamHI. This fragment contains 782 bases upstream of the site of initiation of transcription and 33 bases downstream. The ends of this fragment are filled by the Klenow enzyme and the DNA is inserted at the XbaI site of the vector pLACF, also filled by the Klenow enzyme. This is therefore an unforced cloning. The direction of insertion is assessed by restriction mapping. A plasmid containing the promoter in the correct orientation with respect to the LacZ gene was selected. The sequence of the promoter as well as that of the junctions with the plasmid were checked.

2) This construct called IIbLac, was transfected into two human cell lines:

the HEL and K562 lines;

The plasmid IIbLac was transfected into the HEL and K562 cells by electroporation using the BIORAD "GENE PULSER" apparatus.

HEL cells: $10^7$ cells in PBS, 50 mM Hepes; 10 µg of plasmid IIbLac; 400 volts; 960 µFarads.

K562 cells: $1.5 \times 10^7$ cells, same buffer, 15 µg of plasmid IIbLac, 400 volts, 960 µFarads.

3) After transfection, the cells are cultured for 48 hours in RPMI, 10% FCS.

The cells are then fixed with acetone and stained with 5-bromo-chloro-3-indolyl-β-D-Galactopyranoside (X Gal).

The slides are then examined under a microscope.

HEL cells: 10 slides examined, on each slide, 1 to 5% of the cells are blue.

K562 cells: 10 slides examined, no blue cell.

As control, a transfection was carried out using the LacZ gene placed under the control of the strong and ubiquitous R.S.V. promoter. For both types of cells, 1 to 5% of the cells are blue.

This indicates that this region of the GPIIb promoter contains elements capable of directing the tissue-specific expression of a reporter gene.

This same construct, digested with the restriction enzymes KpnI and BgIII in order to remove the plasmid sequences, was introduced into mouse oocytes in order to produce transgenic mouse lines.

As evident from the above, the invention is not in the least limited to the implementations, embodiments and applications which have just been described more explicitly; on the contrary, it embraces all the variants which may come to the mind of a specialist in this field without departing from the framework or the scope of the present invention.

We claim:

1. A mutant human GPIIb promoter of the formula 5'-X-Y-Z-3', where:

X is a double-stranded DNA consisting of a sequence from position −813 to position −171 of the human GPIIb promoter, or a fragment thereof comprising the sequence from position −598 to position −171, Y is a 97 base pair-long double-stranded DNA from position −170 to position −73 of the human GPIIb promoter, wherein a sequence from position −102 to position −83 of the human GPIIb promoter is a sequence other than a sequence of the formula Sequence ID NO. 3:

5' GCCCTTTGCTCTGCCCGTTG 3'
3' CGGGAAACGAGACGGGCAAC 5' and

Z is a double-stranded DNA consisting of a sequence from position −72 to position −1 of the human GPIIb promoter.

2. The mutant human GPIIb promoter of claim 1, wherein a sequence from position −107 to position −78 the human GPIIb promoter is a sequence other than a sequence of the formula Sequence ID NO. 4:

5' CTATAGCCCTTTGCTCTGCCCGTTGCTCAG 3'
3' GATATCGGGAAACGAGACGGGCAACGAGTC 5'.

3. The mutant human GPIIb promoter of claim 1, wherein a sequence from position −170 to position −103 is a sequence from position −170 to position −103 of the human GPIIb promoter, and a sequence from position −82 to position −73 is a sequence from position −82 to position −73 of the human GPIIb promoter.

4. The mutant human GPIIb promoter of claim 2, wherein a sequence from position −170 to position −108 is a sequence from position −170 to position −108 of the human GPIIb promoter, and a sequence from position −77 to position −73 is a sequence from position −77 to position −73 of the human GPIIb promoter 5. A recombinant vector comprising the mutant human GPIIb promoter of claim 1, 2, 3 or 4, and a gene expressed under the control of said mutant promoter.

6. A method of selectively enhancing expression of a gene in a cell selected from the group consisting of erythrocytic cell lines and megakaryotic cell lines, comprising transforming said cell with the recombinant vector of claim 5.

7. A transformed erythrocytic or non-megakaryocytic cell containing the recombinant vector of claim 5.

8. A recombinant vector comprising an isolated DNA having Sequence ID NO. 1:

5' TCCTAGAAGGAGGAAGTGGGTAAATG 3'
3' AGGATCTTCCTCCTTCACCCATTTAC 5' and Sequence ID NO. 2:

5' CTCAGGTTTTATCGGGGGCAGCAGCT 3'
3' GAGTCCAAAATAGCCCCCGTCGTCGA 5' downstream from Sequence ID NO. 1, a promoter and a gene expressed under the control of said promoter, wherein said recombinant vector:

(a) selectively enhances expression of said gene in an erythrocytic cell line or a megakaryocytic cell line, and (b) does not contain Sequence ID NO. 3:

5' GCCCTTTGCTCTGCCCGTTG 3'
3' CGGGAAACGAGACGGGCAAC 5'.

9. A transformed cell containing the recombinant vector of claim 8.

10. The recombinant vector of claim 8, wherein said DNA consists of a sequence situated between positions −599 and −405 of the GPIIb promoter.

11. A method of selectively enhancing expression of a gene in a cell selected from the group consisting of erythrocytic cell lines and megakaryotic cell lines, comprising transforming said cell with the recombinant vector of claim 8.

12. A recombinant vector comprising the DNA of the formula Sequence ID NO. 3:

5' GCCCTTTGCTCTGCCCGTTG 3'
3' CGGGAAACGAGACGGGCAAC 5', a promoter and a gene expressed Under the control of said promoter, wherein said recombinant vector selectively decreases or suppresses the expression of said gene in a non-megakaryocytic cell line.

13. The recombinant vector of claim 12, wherein said DNA of the formula Sequence ID NO. 3 comprises DNA of the formula Sequence ID NO. 4:

5' CTATAGCCCTTTGCTCTGCCCGTTGCTCAG 3'
3' GATATCGGGAAACGAGACGGGCAACGAGTC 5'.

14. A method of selectively decreasing or suppressing expression of a gene in a non-megakaryotic cell, comprising transforming said cell with the recombinant vector of claim 13.

15. The method of claim 14, wherein said non-megakaryocytic cell line is an erythrocytic cell line.

16. The recombinant vector of claim 12, not containing at least one sequence selected from the group consisting of Sequence ID NO. 1:

5' TCCTAGAAGGAGGAAGTGGGTAAATG 3'
3' AGGATCTTCCTCCTTCACCCATTTAC 5' and Sequence ID NO. 2:

5' CTCAGGTTTTATCGGGGGCAGCAGCT 3'
3' GAGTCCAAAATAGCCCCCGTCGTCGA 5'.

17. A method of selectively decreasing or suppressing expression of a gene in a non-megakaryotic cell, comprising transforming said cell with the recombinant vector of claim 16.

18. A method of selectively decreasing or suppressing expression of a gene in a non-megakaryotic cell, comprising transforming said cell with the recombinant vector of claim 12.

19. The method of claim 18, wherein said non-megakaryocytic cell line is an erythrocytic cell line.

20. A transformed cell containing the recombinant vector of claim 12.

21. A transformed cell obtained by the method of claim 6, 11, 18 or 14.

22. An isolated DNA consisting essentially of a silencer sequence from a GPIIb promoter.

* * * * *

UNITED STATES PATENT AND TRADEMARK OFFICE
CERTIFICATE OF CORRECTION

PATENT NO. : 5,565,358
DATED : October 15, 1996
INVENTOR(S) : Gerard M. DE ROTROU, et al.

It is certified that error appears in the above-indentified patent and that said Letters Patent is hereby corrected as shown below:

On the title page, Item [75], The second inventor's residence should read:

-- Grenoble --

Signed and Sealed this

Tenth Day of December, 1996

Attest:

BRUCE LEHMAN

Attesting Officer

Commissioner of Patents and Trademarks

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 26 base pairs
        ( B ) TYPE: nucleic acid
        ( C ) STRANDEDNESS: double
        ( D ) TOPOLOGY: unknown ( i i ) MOLECULE TYPE: DNA (genomic)

( x i ) SEQUENCE DESCRIPTION: SEQ ID NO:1:

TCCTAGAAGG AGGAAGTGGG TAAATG        2 6

( 2 ) INFORMATION FOR SEQ ID NO:2:

( i ) SEQUENCE CHARACTERISTICS:
        ( A ) LENGTH: 26 base pairs
        ( B ) TYPE: nucleic acid
        ( C ) STRANDEDNESS: double
        ( D ) TOPOLOGY: unknown ( i i ) MOLECULE TYPE: DNA (genomic)

( x i ) SEQUENCE DESCRIPTION: SEQ ID NO:2:

CTCAGGTTTT ATCGGGGGCA GCAGCT        2 6

( 2 ) INFORMATION FOR SEQ ID NO:3:

( i ) SEQUENCE CHARACTERISTICS:
        ( A ) LENGTH: 20 base pairs
        ( B ) TYPE: nucleic acid
        ( C ) STRANDEDNESS: double
        ( D ) TOPOLOGY: unknown ( i i ) MOLECULE TYPE: DNA (genomic)

( x i ) SEQUENCE DESCRIPTION: SEQ ID NO:3:

GCCCTTTGCT CTGCCCGTTG        2 0

( 2 ) INFORMATION FOR SEQ ID NO:4:

( i ) SEQUENCE CHARACTERISTICS:

(A) LENGTH: 30 base pairs
(B) TYPE: nucleic acid
(C) STRANDEDNESS: double
(D) TOPOLOGY: unknown (i i) MOLECULE TYPE: DNA (genomic)

(x i) SEQUENCE DESCRIPTION: SEQ ID NO:4:

CTATAGCCCT TTGCTCTGCC CGTTGCTCAG                30